United States Patent
Hsu et al.

(10) Patent No.: US 10,052,063 B2
(45) Date of Patent: Aug. 21, 2018

(54) SENSING BONE FIXING ELEMENT

(71) Applicants: National Chiao Tung University, Hsinchu (TW); National Taiwan University Hospital Hsin-Chu Branch, Hsinchu (TW)

(72) Inventors: Wen-Syang Hsu, Hsinchu (TW); Tze-Hong Wong, Hsinchu (TW); Asher Sun, Taipei (TW); Sung-Yueh Wu, Chiayi County (TW)

(73) Assignees: National Chiao Tung University, Hsinchu (TW); National Taiwan University Hospital Hsin-Chu Branch, Hsinchu (TW)

( * ) Notice: Subject to any disclaimer, the term of this patent is extended or adjusted under 35 U.S.C. 154(b) by 352 days.

(21) Appl. No.: 14/985,458

(22) Filed: Dec. 31, 2015

(65) Prior Publication Data

US 2017/0112436 A1    Apr. 27, 2017

(30) Foreign Application Priority Data

Oct. 23, 2015   (TW) .............................. 104134807 A

(51) Int. Cl.
*A61B 5/00* (2006.01)
*A61B 17/70* (2006.01)
*A61B 5/07* (2006.01)

(52) U.S. Cl.
CPC ............ *A61B 5/4851* (2013.01); *A61B 5/076* (2013.01); *A61B 5/686* (2013.01); *A61B 17/7032* (2013.01); *A61B 2562/0261* (2013.01)

(58) Field of Classification Search
CPC ......... A61B 5/00; A61B 5/4851; A61B 5/076; A61B 5/686; A61B 5/70
See application file for complete search history.

(56) References Cited

U.S. PATENT DOCUMENTS

| 3,151,258 | A | | 9/1964 | Sonderegger et al. |
| 4,738,146 | A | | 4/1988 | Baumgartner et al. |
| 5,222,399 | A | | 6/1993 | Kropp |
| 6,134,947 | A | * | 10/2000 | Kwun ...................... G01L 1/14 |
| | | | | 280/735 |
| 6,656,135 | B2 | * | 12/2003 | Zogbi .................. A61B 5/0031 |
| | | | | 128/897 |

(Continued)

FOREIGN PATENT DOCUMENTS

| TW | 476633 | 2/2002 |
| TW | M334573 | 6/2008 |

OTHER PUBLICATIONS

Goldstein et al., "When is a spine fused?" Injury, Mar. 2011, pp. 306-313.

(Continued)

*Primary Examiner* — Christopher Beccia
(74) *Attorney, Agent, or Firm* — JCIPRNET

(57) ABSTRACT

A sensing bone fixing element includes a fixing portion, a fastening portion, a capacitor structure, and a coil. The fastening portion is fixed to the fixing portion and suitable for being fastened to a bone. The fastening portion passes through the capacitor structure which has a capacitance value and includes a first conductive layer, a second conductive layer, and an elastic dielectric layer. The first conductive layer leans against the fixing portion, the second conductive layer leans against the bone, and the elastic dielectric layer is located between the first conductive layer and the second conductive layer. The coil has an inductance value, and two ends of the coil are respectively connected to the first conductive layer and the second conductive layer. The coil receives a detection radio frequency (RF) signal and generates a responding RF signal according to variations in the capacitance value and the inductance value.

12 Claims, 7 Drawing Sheets

(56) References Cited

U.S. PATENT DOCUMENTS

| | | | |
|---|---|---|---|
| 8,016,859 B2 * | 9/2011 | Donofrio | A61B 5/0031 |
| | | | 606/246 |
| 8,622,936 B2 | 1/2014 | Schenberger et al. | |
| 9,451,919 B2 * | 9/2016 | Roche | A61B 5/0031 |
| 2010/0268119 A1 * | 10/2010 | Morrison | A61B 17/7091 |
| | | | 600/587 |
| 2014/0275959 A1 * | 9/2014 | Disegi | A61B 17/6466 |
| | | | 600/410 |

OTHER PUBLICATIONS

Murakami et al., "Feasibility of novel four degrees of freedom capacitive force sensor for skin interface force," BioMedical Engineering OnLine, Nov. 2012, pp. 1-18.

Paydar et al., "Fabrication of a Thin-film Capacitive Force Sensor Array for Tactile Feedback in Robotic Surgery," 34th Annual International Conference of the IEEE EMBS, Aug. 2012, pp. 2355-2358.

Dobrzynska et al., "Polymer-based flexible capacitive sensor for three-axial force measurements," Journal of Micromechanics and Microengineering, Nov. 2012, pp. 1-11.

Chen et al., "Microfabricated Implantable Parylene-Based Wireless Passive Intraocular Pressure Sensors," Journal of Microelectromechanical Systems, Dec. 2008, pp. 1342-1351.

Zhai et al., "Design and modelling of a passive wireless pressure sensor," CIRP Annals—Manufacturing Technology, Apr. 2010, pp. 187-190.

Luo et al., "A Microfabricated Wireless RF Pressure Sensor Made Completely of Biodegradable Materials," Journal of Microelectromechanical Systems, Feb. 2014, pp. 4-13.

* cited by examiner

SENSING BONE FIXING ELEMENT

CROSS-REFERENCE TO RELATED APPLICATION

This application claims the priority benefit of Taiwan application serial no. 104134807, filed on Oct. 23, 2015. The entirety of the above-mentioned patent application is hereby incorporated by reference herein and made a part of this specification.

TECHNICAL FIELD

The disclosure relates to a bone fixing element; more particularly, the disclosure relates to a sensing bone fixing element.

DESCRIPTION OF RELATED ART

In the field of orthopedics, pedicle screws are often applied to fix vertebras, so as to enhance the spine strength of patients who suffer from osteoporosis. If, due to external forces, the pedicle screws are loosened during the surgical operation or during rehabilitation after the operation, the performance of fixing the vertebras may be reduced, and thereby the effects of spine fusion may be lessened.

After the surgical operation, the existing detection method can merely be applied through photographing the affected regions of the patients with use of X-rays, so as to observe the X-ray photographs to learn how the pedicle screws are fixed. However, said detection method is not accurate if it is treated within a short period of time or if it is performed several times in an intense manner, and the patients may be exposed to excessive radiation.

SUMMARY

The disclosure is directed to a sensing bone fixing element that can be applied to learn how tight a fixing element and a bone are fixed together without using radiation.

In an embodiment of the disclosure, a sensing bone fixing element that includes a fixing portion, a fastening portion, a capacitor structure, and a coil is provided. The fastening portion is fixed to the fixing portion and suitable for being fastened to a bone. The fastening portion passes through the capacitor structure which has a capacitance value and includes a first conductive layer, a second conductive layer, and an elastic dielectric layer. The first conductive layer leans against the fixing portion. The second conductive layer leans against the bone. The elastic dielectric layer is located between the first conductive layer and the second conductive layer. The coil has an inductance value, and two ends of the coil are respectively connected to the first conductive layer and the second conductive layer. After the coil receives a detection radio frequency (RF) signal, the coil generates a responding RF signal according to variations in the capacitance value and the inductance value.

According to an embodiment of the disclosure, a thickness of the elastic dielectric layer is positively correlated to a distance between the first conductive layer and the second conductive layer.

According to an embodiment of the disclosure, a frequency of the responding RF signal is positively correlated to a distance between the first conductive layer and the second conductive layer.

According to an embodiment of the disclosure, when a stress exerted by the fixing portion on the capacitor structure decreases, the elastic dielectric layer deforms, such that a distance between the first conductive layer and the second conductive layer increases.

According to an embodiment of the disclosure, the coil is located between the first conductive layer and the second conductive layer, the coil has an opening, and the elastic dielectric layer is located in the opening.

According to an embodiment of the disclosure, the coil is located on one side of the fixing portion away from the fastening portion.

According to an embodiment of the disclosure, the coil senses the detection RF signal of a sensing element through a wireless connection.

According to an embodiment of the disclosure, the inductance value of the coil is a fixed inductance value.

According to an embodiment of the disclosure, the fixing portion and the fastening portion define a pedicle screw.

According to an embodiment of the disclosure, a material of the capacitor structure is a biocompatible material.

According to an embodiment of the disclosure, a material of the coil is a biocompatible material.

According to an embodiment of the disclosure, a thickness of the capacitor structure is within a range from 0.1 millimeters to 10 millimeters.

In view of the above, the sensing bone fixing element provided herein has the capacitor structure and the coil; hence, after the coil receives the detection RF signal, the coil generates the responding RF signal according to the variations in the inductance value of the coil and the capacitance value of the capacitor structure, and the degree of variations in the tightness of fastening the sensing bone fixing element to the bone can accordingly be calculated. According to the related art, the affected region of the patient is photographed with use of X-rays, and the condition of fixing the pedicle screw to the bone can be learned by observing the photographs; by contrast, the degree of variations in the tightness of fastening the sensing bone fixing element to the bone can be detected without using radiation, and the detection result is accurate and can be obtained with ease in an efficient manner.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1A:
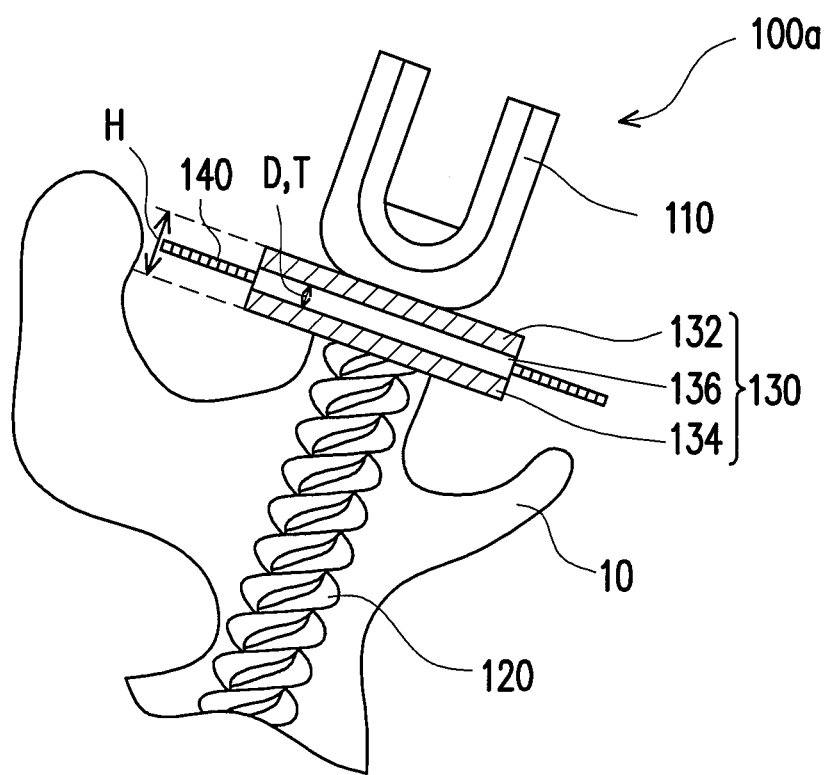
FIG. 1A is a schematic diagram illustrating a sensing bone fixing element fixed to a bone according to an embodiment of the disclosure.
Figure 1B:
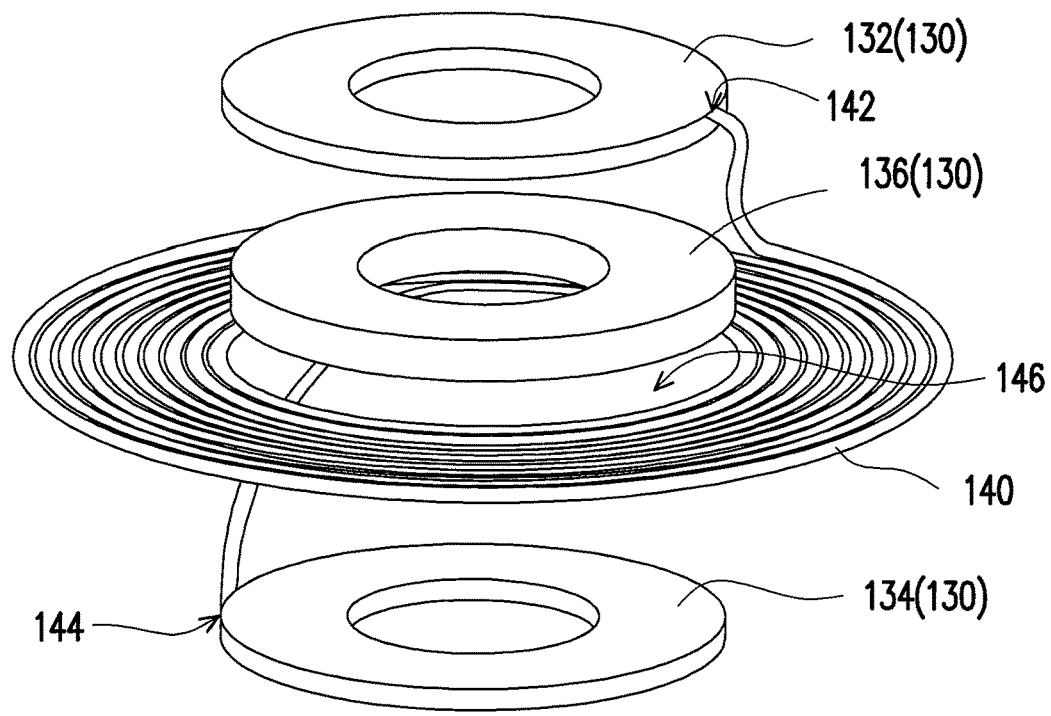
FIG. 1B is a schematic exploded diagram illustrating a capacitor structure and a coil of the sensing bone fixing element depicted in FIG. 1A.
Figure 1C:
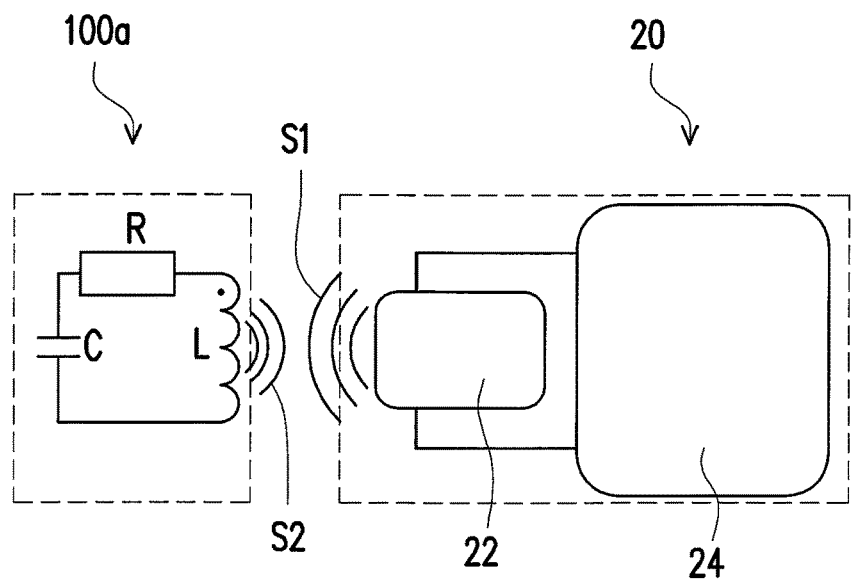
FIG. 1C is a schematic circuit diagram illustrating the sensing bone fixing element depicted in FIG. 1A and a sensing element.

FIG. 1A is a schematic diagram illustrating a sensing bone fixing element fixed to a bone according to an embodiment of the disclosure. FIG. 1B is a schematic exploded diagram illustrating a capacitor structure and a coil of the sensing bone fixing element depicted in FIG. 1A. FIG. 1C is a schematic circuit diagram illustrating the sensing bone fixing element depicted in FIG. 1A and a sensing element. With reference to FIG. 1A, FIG. 1B, and FIG. 1C, a sensing bone fixing element 100a provided in the present embodiment includes a fixing portion 110, a fastening portion 120, a capacitor structure 130, and a coil 140. The fastening portion 120 is fixed to the fixing portion 110 and suitable for being fastened to a bone 10. The fastening portion 120 passes through the capacitor structure 130 which has a capacitance value C and includes a first conductive layer 132, a second conductive layer 134, and an elastic dielectric layer 136. The first conductive layer 132 leans against the fixing portion 110, the second conductive layer 134 leans against the bone 10, and the elastic dielectric layer 136 is located between the first conductive layer 132 and the second conductive layer 134. The coil 140 has an inductance value L, and two ends 142 and 144 of the coil 140 are respectively connected to the first conductive layer 132 and the second conductive layer 134. After the coil 140 receives a detection RF signal S1, the coil 140 generates a responding RF signal S2 according to variations in the capacitance value C and the inductance value L.

Specifically, in the present embodiment, the fixing portion 110 and the fastening portion 120 define a pedicle screw, and the fastening portion 120 is suitable for being fastened to the bone 10 (e.g., including but not limited to the vertebra). A material of the capacitor structure 130 is a biocompatible material, such as a metallic conductive material (e.g., titanium, gold, platinum, or an oxide of the above), a non-metallic conductive material (e.g., iridium oxide or graphite), and a non-conductive material (e.g., polydimethylsiloxane (PDMS)). Since the capacitor structure 130 provided in the present embodiment has the elastic dielectric layer 136, the distance D between the first conductive layer 132 and the second conductive layer 134 does not remain constant but may be changed together with deformation (e.g., contraction or extension) of the elastic dielectric layer 136. Namely, the capacitance value C of the capacitor structure 130 provided herein is a variable capacitance value and may be changed together with the distance D between the first conductive layer 132 and the second conductive layer 134. Preferably, the thickness H of the capacitor structure 130 is within a range from 0.1 millimeters (mm) to 10 mm, for instance.

A material of the coil 140 is a biocompatible material, such as a metallic conductive material (e.g., titanium, gold, platinum, or an oxide of the above) and a non-metallic conductive material (e.g., iridium oxide or graphite). Here, the number of windings in the coil 140 remains unchanged, and therefore the inductance value L of the coil 140 is a fixed inductance value. Two ends 142 and 144 of the coil 140 are respectively connected to the first conductive layer 132 and the second conductive layer 134 by using the biocompatible material to encapsulate and fix with the first conductive layer 132 and the second conductive layer 134. As shown in FIG. 1A and FIG. 1B, the coil 140 is located between the first conductive layer 132 and the second conductive layer 134, the coil 140 has an opening 146, and the elastic dielectric layer 136 is located in the opening 146. That is, the coil 140 is sandwiched between the first conductive layer 132 and the second conductive layer 134 of the capacitor structure 130, which should however not be construed as a limitation to the disclosure. In another embodiment, with reference to FIG. 1D, the coil 140b of the sensing bone fixing element 100b is located on one side of the fixing portion 110 away from the fastening portion 120. Here, the coil 140b is clamped by two fixing elements 150a and 150b and leans against the fixing portion 110, and the coil 140b and the fixing elements 150a and 150b are fixed by a fixing element 150c. That is, the fixing portion 110 is located between the coil 140b and the capacitor structure 130; in other words, the coil 140b is close to the outside of the human body and can easily receive the detection RF signal S1.

Figure 1D:
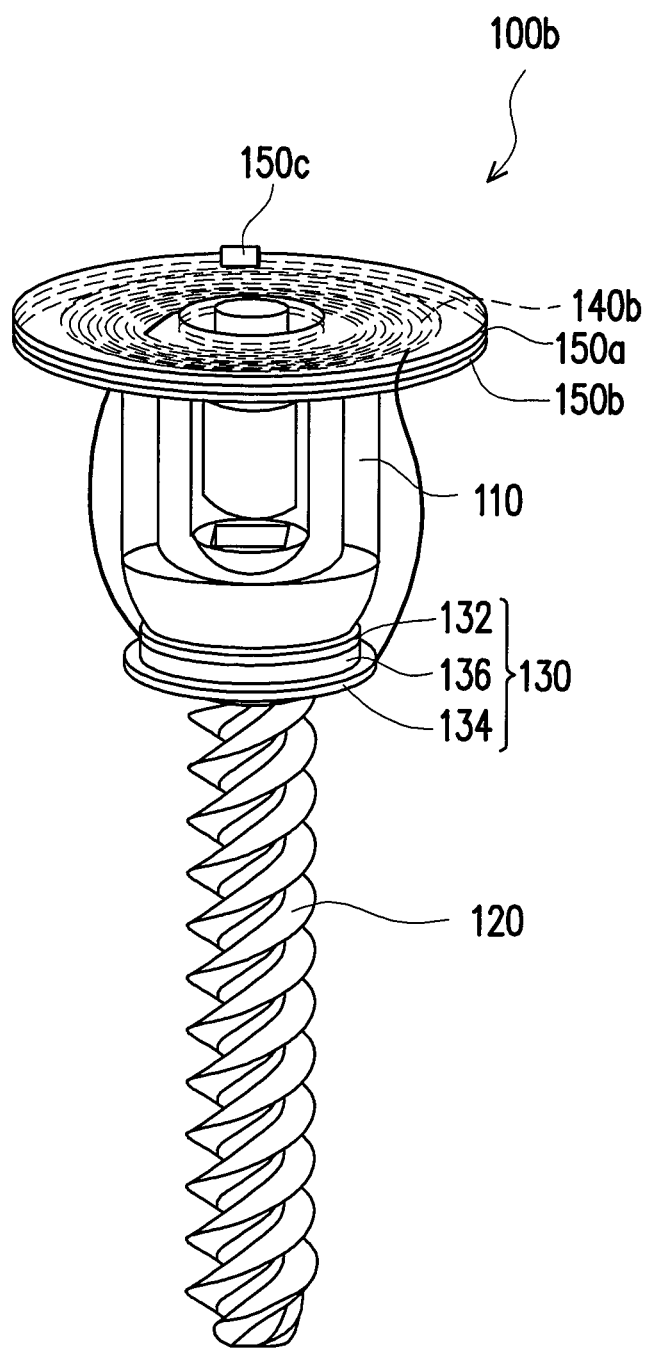
FIG. 1D is a schematic diagram illustrating a sensing bone fixing element according to another embodiment of the disclosure.

It should be mentioned that the size of the first and second conductive layers 132 and 134 is not limited herein. In FIG. 1A and FIG. 1B, the size of the first conductive layer 132 is substantially the same as the size of the second conductive layer 134; alternatively, as shown in FIG. 1D, the size of the first conductive layer 132 (e.g., the area of the first conductive layer 132) is substantially smaller than the size of the second conductive layer 134 (e.g., the area of the second conductive layer 134). In other embodiments that are not shown herein, the size of the first conductive layer 132 (e.g., the area of the first conductive layer 132) is substantially greater than the size of the second conductive layer 134 (e.g., the area of the second conductive layer 134). All of the above fall within the scope of protection provided herein.

Figure 2:
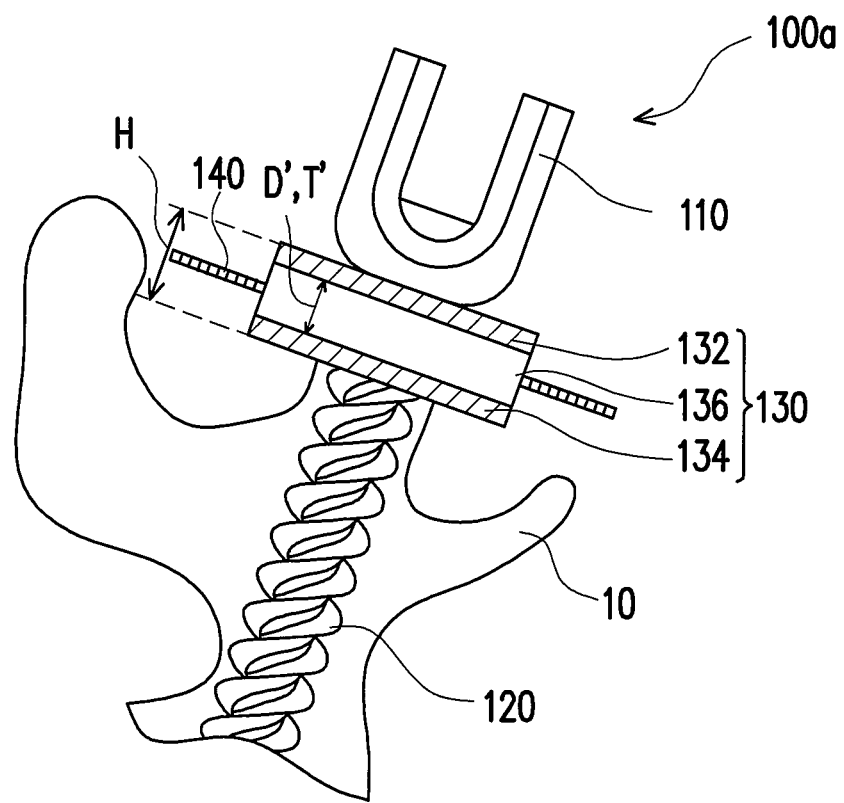
FIG. 2 is a schematic circuit diagram illustrating that the sensing bone fixing element depicted in FIG. 1A is not fastened to a bone.

With reference to FIG. 1A and FIG. 1C, during surgical operation, the sensing bone fixing element 100a may be fastened to the bone 10. Namely, the fixing portion 110 exerts a stress on the capacitor structure 130, such that the first conductive layer 132 of the capacitor structure 130 leans against the fixing portion 110, the second conductive layer 134 leans against the bone 10, and the elastic dielectric layer 136 located between the first conductive layer 132 and the second conductive layer 134 deforms (contracts) because of the stress. Here, the thickness of the elastic dielectric layer 136 is defined as the thickness T when the sensing bone fixing element 100a is fastened to the bone 10, and the distance D from the first conductive layer 132 to the second conductive layer 134 is defined as an initial distance. With reference to FIG. 1A, FIG. 1C, and FIG. 2, during rehabilitation after the surgical operation, the stress exerted by the fixing portion 110 on the capacitor structure 130 may decrease due to improper movements during rehabilitation after the surgical operation or due to the loose bone 10, such that the elastic dielectric layer 136 may deform (extend), i.e., the thickness T of the elastic dielectric layer 136 becomes the thickness T' when the sensing bone fixing element 100a is no longer fastened to the bone 10. At this time, the initial distance D from the first conductive layer 132 to the second conductive layer 134 becomes a distance D'. At this time, paramedics may send the detection RF signal S1 through a sensing element 20, and the coil 140 within the human body may, through wireless connections, receive the detection RF signal S1 coming from the sensing element 20 outside the human body. After receiving the detection RF signal S1, the coil 140 may generate the responding RF signal S2 and provide the same to the sensing element 20 according to the variations in the capacitance value C of the capacitor structure 130 and the inductance value L of the coil 140. Here, after receiving the responding RF signal S2, a sensor antenna 22 in the sensing element 20 may obtain a frequency through an analysis by a frequency spectrum analyzer 24. If the obtained frequency is compared with data in a quantization table of the tightness of the screw, it can be learned that the sensing bone fixing element 100a is no longer tightly fastened to the bone 10.

Figure 3:
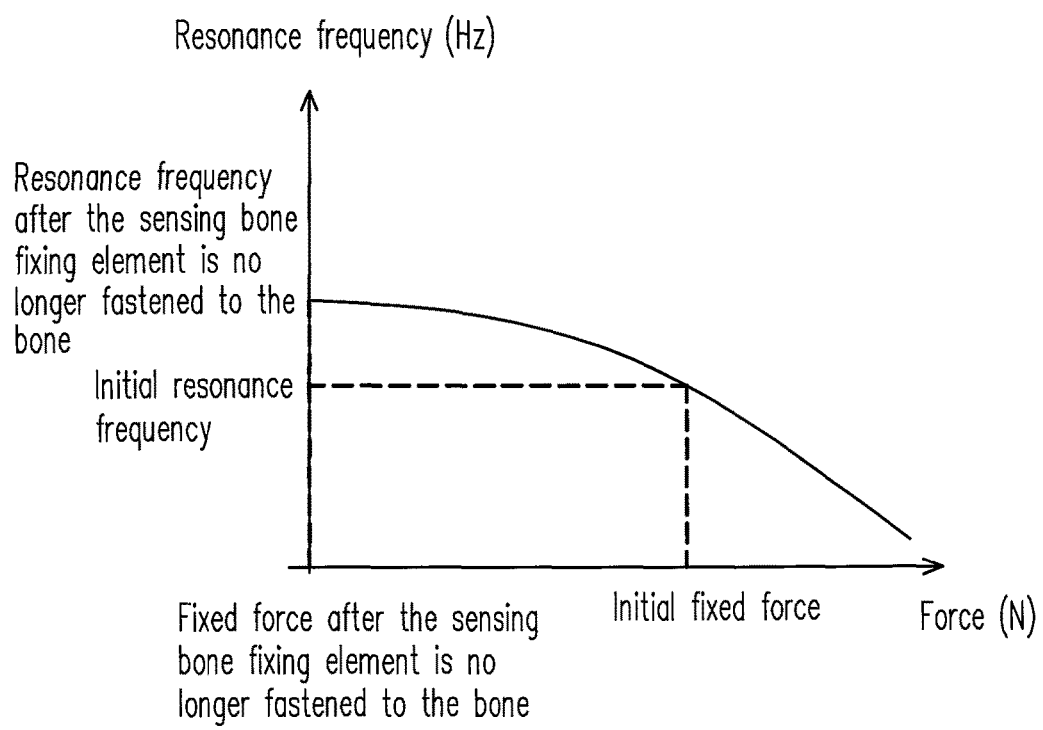
FIG. 3 is a schematic curve illustrating a resonance frequency and a fastening force of a sensing bone fixing element fastened to a bone.

In particular, the inductance value L of the coil 140 is a fixed value according to the present embodiment; therefore, if the capacitance value C of the capacitor structure 130 decreases (i.e., the thickness T of the elastic dielectric layer 136 becomes the thickness T' when the sensing bone fixing element 100a is no longer fastened to the bone 10; the initial distance D from the first conductive layer 132 and the second conductive layer 134 becomes the distance D'), the frequency of the responding RF signal S2 appears to increase according to the equation $$f = \frac{1}{2\pi\sqrt{LC}},$$

as shown in FIG. 3. That is, the thickness T of the elastic dielectric layer 136 is positively correlated to the distance D between the first conductive layer 132 and the second conductive layer 134, and the frequency of the responding RF signal S2 is positively correlated to the distance D between the first conductive layer 132 and the second conductive layer 134 as well. In the present embodiment, the sensing bone fixing element 100a has the capacitor structure 130 and the coil 140; hence, after the coil 140 receives the detection RF signal S1, the coil 140 generates the responding RF signal S2 according to the variations in the inductance value L of the coil 140 and the capacitance value C of the capacitor structure 130, and the degree of variations in the tightness of fastening the sensing bone fixing element 100a to the bone 10 can accordingly be calculated. According to the related art, the affected region of the patient is photographed with use of X-rays, and the condition of fixing the pedicle screw to the bone can be learned by observing the photographs; by contrast, the degree of variations in the tightness of fastening the sensing bone fixing element 100a to the bone 10 can be passively detected without using radiation, and the detection result is accurate and can be obtained with ease in an efficient manner.

Figure 4A:
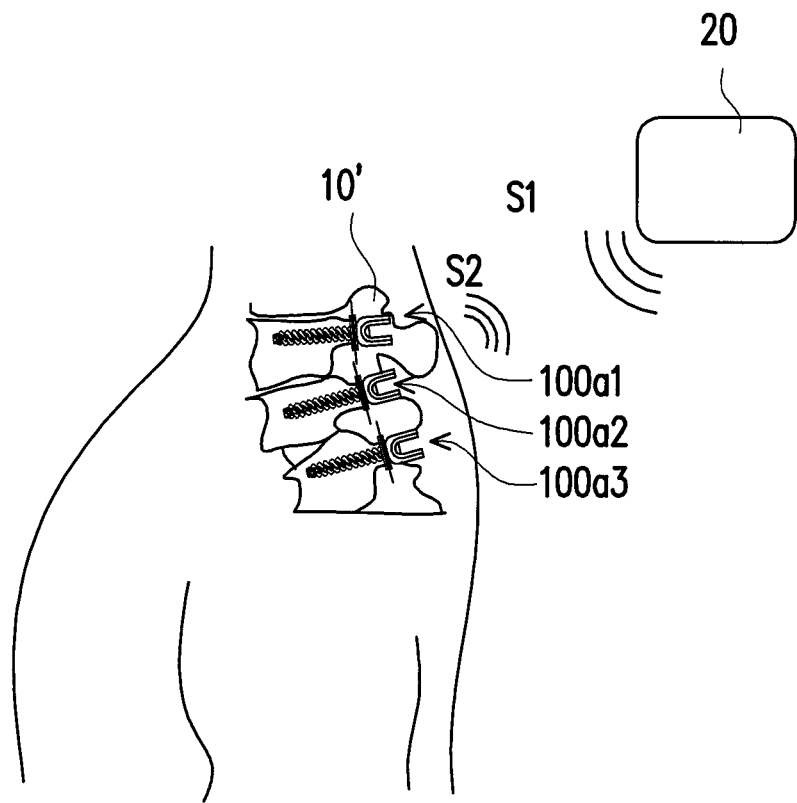
FIG. 4A is a schematic diagram illustrating plural sensing bone fixing elements fastened to a human body.
Figure 4B:
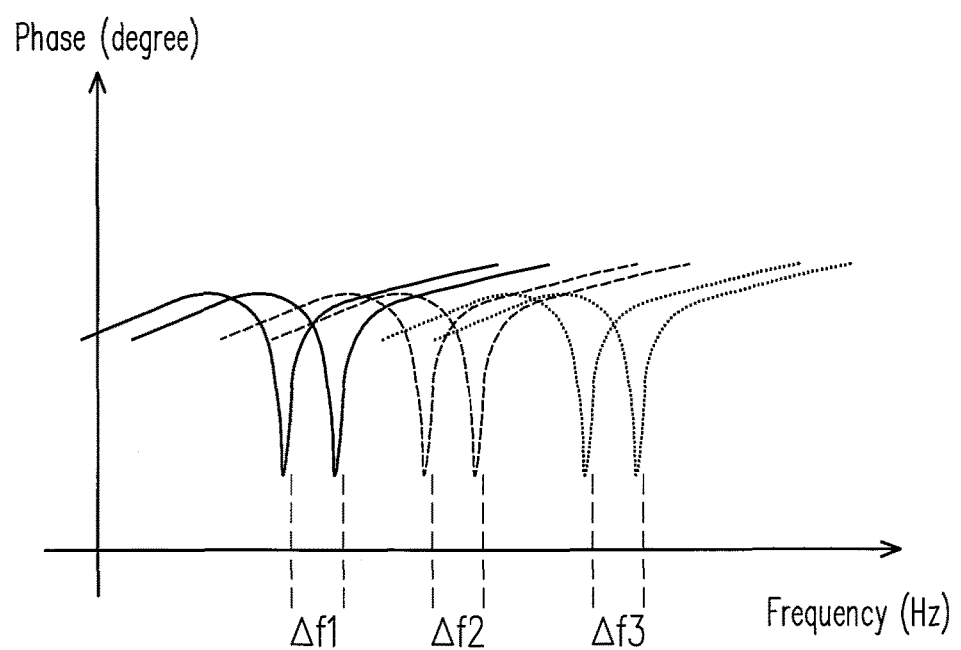
FIG. 4B is a schematic curve illustrating a phase and a frequency of a responding RF signal generated by the coil shown in FIG. 4A.

FIG. 4A is a schematic diagram illustrating that plural sensing bone fixing elements depicted in FIG. 1A are fastened to a human body. FIG. 4B is a schematic curve illustrating a phase and a frequency of a responding RF signal generated by the coil shown in FIG. 4A. With reference to FIG. 4A and FIG. 4B, in the present embodiment, the sensing bone fixing elements 100a1, 100a2, and 100a3 are fastened to the bone 10'. The sensing bone fixing elements 100a1, 100a2, and 100a3 are similar to the sensing bone fixing element 100a depicted in FIG. 1A, and the difference therebetween lies in the capacitance value of the capacitor structure 130 (shown in FIG. 1A) and the inductance value of the coil 140 (shown in FIG. 1A) of each of the sensing bone fixing elements 100a1, 100a2, and 100a3. With reference to FIG. 1C, by changing the inductance value L of the coil 140 of each of the sensing bone fixing elements 100a1, 100a2, and 100a3 or the capacitance value C of the capacitor structure 130, the widths Δf1, Δf2, and Δf3 of the frequencies of the sensing bone fixing elements 100a1, 100a2, and 100a3 are separated and not overlapped. As a result, the degree of variations in the tightness of fastening the sensing bone fixing elements 100a1, 100a2, and 100a3 at different locations to the bone 10' can be detected simultaneously.

To sum up, the sensing bone fixing element provided herein has the capacitor structure and the coil; hence, after the coil receives the detection RF signal, the coil generates the responding RF signal according to the variations in the inductance value of the coil and the capacitance value of the capacitor structure, and the degree of variations in the tightness of fastening the sensing bone fixing element to the bone can accordingly be calculated. According to the related art, the affected region of the patient is photographed with use of X-rays, and the condition of fixing the pedicle screw to the bone can be learned by observing the photographs; by contrast, the degree of variations in the tightness of fastening the sensing bone fixing element to the bone can be passively detected without using radiation, and the detection result is accurate and can be obtained with ease.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A sensing bone fixing element comprising:
   a fixing portion;
   a fastening portion fixed to the fixing portion, the fastening portion being suitable for being fastened to a bone;
   a capacitor structure, the fastening portion passing through the capacitor structure and having a capacitance value, the capacitor structure comprising:
      a first conductive layer leaning against the fixing portion;
      a second conductive layer configured to lean against the bone; and
      an elastic dielectric layer located between the first conductive layer and the second conductive layer; and
   a coil having an inductance value, two ends of the coil being respectively connected to the first conductive layer and the second conductive layer, wherein after the coil receives a detection radio frequency signal, the coil generates a responding radio frequency signal according to variations in the capacitance value and the inductance value.

2. The sensing bone fixing element as recited in claim 1, wherein a thickness of the elastic dielectric layer is positively correlated to a distance between the first conductive layer and the second conductive layer.

3. The sensing bone fixing element as recited in claim 1, wherein a frequency of the responding radio frequency signal is positively correlated to a distance between the first conductive layer and the second conductive layer.

4. The sensing bone fixing element as recited in claim 1, wherein when a stress exerted by the fixing portion on the capacitor structure decreases, the elastic dielectric layer deforms, such that a distance between the first conductive layer and the second conductive layer increases.

5. The sensing bone fixing element as recited in claim 1, wherein the coil is located between the first conductive layer and the second conductive layer, the coil has an opening, and the elastic dielectric layer is located in the opening.

6. The sensing bone fixing element as recited in claim 1, wherein the coil is located on one side of the fixing portion away from the fastening portion.

7. The sensing bone fixing element as recited in claim 1, wherein the coil senses the detection radio frequency signal of a sensing element through a wireless connection.

8. The sensing bone fixing element as recited in claim 1, wherein the inductance value of the coil is a fixed inductance value.

9. The sensing bone fixing element as recited in claim 1, wherein the fixing portion and the fastening portion define a pedicle screw.

10. The sensing bone fixing element as recited in claim 1, wherein a material of the capacitor structure is a biocompatible material.

11. The sensing bone fixing element as recited in claim 1, wherein a material of the coil is a biocompatible material.

12. The sensing bone fixing element as recited in claim 1, wherein a thickness of the capacitor structure is within a range from 0.1 millimeters to 10 millimeters.

* * * * *